(12) United States Patent
Jurevicius et al.

(10) Patent No.: US 12,096,915 B2
(45) Date of Patent: Sep. 24, 2024

(54) SHEATH LOCATION INDICATOR AND OVEREXTENSION PREVENTER

(71) Applicant: GYRUS ACMI, INC, Westborough, MA (US)

(72) Inventors: Christine N. Jurevicius, Issaquah, WA (US); Madeline C. Graham, Sammamish, WA (US); Christopher R. Ralph, Woodinville, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 703 days.

(21) Appl. No.: 16/298,046

(22) Filed: Mar. 11, 2019

(65) Prior Publication Data

US 2020/0288952 A1 Sep. 17, 2020

(51) Int. Cl.
| | | |
|---|---|---|
| *A61B 1/01* | (2006.01) | |
| *A61B 1/00* | (2006.01) | |
| *A61B 1/005* | (2006.01) | |
| *A61B 1/267* | (2006.01) | |
| *A61B 8/12* | (2006.01) | |

(52) U.S. Cl.
CPC ............ *A61B 1/01* (2013.01); *A61B 1/00154* (2013.01); *A61B 1/0055* (2013.01); *A61B 1/2676* (2013.01); *A61B 8/12* (2013.01); *A61B 1/00135* (2013.01)

(58) Field of Classification Search
CPC ............ A61B 1/00087; A61B 1/00089; A61B 1/00098; A61B 1/00101; A61B 1/00131; A61B 1/00133; A61B 1/00135; A61B 1/00142; A61B 1/00154; A61B 1/012; A61B 1/0125; A61B 1/018; A61B 1/2676
See application file for complete search history.

(56) References Cited

U.S. PATENT DOCUMENTS

| | | | | |
|---|---|---|---|---|
| 4,646,722 A | * | 3/1987 | Silverstein | A61B 1/00142 600/122 |
| 4,741,326 A | * | 5/1988 | Sidall | A61B 1/00142 600/125 |
| 5,050,585 A | * | 9/1991 | Takahashi | A61B 1/12 600/459 |
| 5,257,617 A | * | 11/1993 | Takahashi | A61B 1/00142 600/128 |
| 5,855,569 A | * | 1/1999 | Komi | A61B 10/04 604/103 |
| 5,882,345 A | * | 3/1999 | Yoon | A61M 25/04 604/105 |
| 5,899,850 A | * | 5/1999 | Ouchi | A61B 10/04 600/104 |
| 7,449,011 B2 | * | 11/2008 | Wenchell | A61B 17/3439 606/198 |

(Continued)

*Primary Examiner* — Ryan N Henderson
(74) *Attorney, Agent, or Firm* — Schwegman Lundberg & Woessner, P.A.

(57) ABSTRACT

An apparatus for controlling advancement of a sheath or a catheter at a distal end of an endoscope. An exemplary apparatus includes a flexible sheath that receives a medical device within an internal lumen and is received within a working channel of an endoscope. The apparatus also includes a component that is at least one of external or internal to the sheath. The component causes a change in longitudinal motion friction of the sheath above a predefined threshold amount as the sheath moves relative to an exit ramp of the endoscope.

13 Claims, 4 Drawing Sheets

(56) References Cited

U.S. PATENT DOCUMENTS

| | | | |
|---|---|---|---|
| 7,520,950 B2* | 4/2009 | Saadat | B29C 66/14 |
| | | | 156/203 |
| 10,687,848 B2* | 6/2020 | Mikol | A61B 17/3421 |
| 10,709,475 B2* | 7/2020 | Mikol | A61B 17/3439 |
| 10,842,556 B1* | 11/2020 | Tandri | A61B 18/1492 |
| 11,647,899 B2* | 5/2023 | DeVries | A61B 1/015 |
| | | | 600/104 |
| 11,918,415 B2* | 3/2024 | Suzuki | A61B 1/00082 |
| 2004/0077927 A1* | 4/2004 | Ouchi | A61B 1/00142 |
| | | | 600/123 |
| 2005/0101836 A1* | 5/2005 | Onuki | A61M 25/09 |
| | | | 600/104 |
| 2005/0119525 A1* | 6/2005 | Takemoto | A61B 1/273 |
| | | | 600/114 |
| 2006/0173241 A1* | 8/2006 | Ouchi | A61B 1/31 |
| | | | 600/128 |
| 2007/0185377 A1* | 8/2007 | Murakami | A61B 17/32056 |
| | | | 600/106 |
| 2007/0208220 A1* | 9/2007 | Carter | A61B 1/00098 |
| | | | 604/165.01 |
| 2007/0208221 A1* | 9/2007 | Kennedy, II | A61B 1/018 |
| | | | 604/165.01 |
| 2007/0244355 A1* | 10/2007 | Shaw | A61B 1/018 |
| | | | 600/107 |
| 2007/0244356 A1* | 10/2007 | Carrillo, Jr. | A61B 1/00098 |
| | | | 600/107 |
| 2007/0249898 A1* | 10/2007 | Otawara | A61B 1/00098 |
| | | | 600/107 |
| 2008/0208127 A1* | 8/2008 | Kuriyama | A61B 1/018 |
| | | | 604/164.01 |
| 2009/0112060 A1* | 4/2009 | Sugiyama | A61B 1/00098 |
| | | | 600/104 |
| 2009/0227835 A1* | 9/2009 | Terliuc | A61B 1/005 |
| | | | 600/106 |
| 2010/0317963 A1* | 12/2010 | Clancy | A61F 2/95 |
| | | | 623/1.11 |
| 2011/0319710 A1* | 12/2011 | Phillips-Hungerford | |
| | | | A61B 17/29 |
| | | | 600/106 |
| 2013/0211176 A1* | 8/2013 | Habib | A61N 7/00 |
| | | | 606/41 |
| 2013/0310684 A1* | 11/2013 | Takachi | A61B 8/4254 |
| | | | 600/424 |
| 2014/0249370 A1* | 9/2014 | Hurst | A61B 1/00135 |
| | | | 600/114 |
| 2015/0080764 A1* | 3/2015 | Poe | A61B 17/3478 |
| | | | 604/506 |
| 2016/0007832 A1* | 1/2016 | Shimada | A61B 1/0125 |
| | | | 604/95.04 |
| 2016/0089125 A1* | 3/2016 | Morimoto | A61B 1/00098 |
| | | | 600/107 |
| 2016/0278809 A1* | 9/2016 | Sato | A61B 1/06 |
| 2016/0367231 A1* | 12/2016 | Uemichi | A61B 1/0051 |
| 2017/0290572 A1* | 10/2017 | Nakata | A61B 1/018 |
| 2018/0168541 A1* | 6/2018 | Kitahara | A61B 8/5261 |
| 2018/0256237 A1* | 9/2018 | Fan | A61B 18/02 |
| 2019/0274729 A1* | 9/2019 | Mikol | A61B 17/3423 |
| 2019/0290105 A1* | 9/2019 | Ralph | A61M 25/008 |
| 2019/0290106 A1* | 9/2019 | Ralph | A61M 25/0662 |
| 2019/0290107 A1* | 9/2019 | Ralph | A61B 1/00098 |
| 2019/0298975 A1* | 10/2019 | Wang | A61B 10/0233 |
| 2020/0100665 A1* | 4/2020 | Eibs | F16H 21/16 |
| 2020/0121359 A1* | 4/2020 | Rokde | A61B 1/00167 |
| 2020/0171292 A1* | 6/2020 | Siuda | A61B 1/018 |
| 2020/0375655 A1* | 12/2020 | Axelsson | A61B 17/3478 |
| 2021/0023386 A1* | 1/2021 | Mamiya | A61B 17/3478 |
| 2022/0054114 A1* | 2/2022 | Brakhya | A61B 1/00068 |
| 2022/0087641 A1* | 3/2022 | Suzuki | A61B 1/00098 |
| 2023/0172435 A1* | 6/2023 | Miller | A61B 1/018 |
| | | | 600/107 |

* cited by examiner

SHEATH LOCATION INDICATOR AND OVEREXTENSION PREVENTER

BACKGROUND

Existing devices that are used for bronchoscopy do not include means of preventing health care professionals (HCPs) from overextending the sheath and potentially damaging the airway walls. Most devices have a set length sheath that can be adjusted slightly to bring the sheath into the view of the endoscopic camera and bring it closer to the target tissue. This set length is adjusted from the handle, but there are no feedback mechanisms to prevent the HCP from overextending the sheath into the tissue. To avoid overextension, some HCPs will set the sheath extension length while the scope is outside of the body. They extend the sheath to the maximum length they feel comfortable with and then lock the sheath at that position. This takes extra time, though, and requires the HCPs to remove the scope from the body, if not done before beginning the procedure.

SUMMARY

The present invention includes an apparatus for controlling advancement of a sheath or a catheter relative to a scope (e.g., endoscope). An exemplary apparatus includes a flexible sheath that receives a medical device within an internal lumen and is received within a working channel of an endoscope, such as a bronchoscope. The apparatus also includes a component that is at least one of external or internal to the sheath. The component causes a change in longitudinal motion friction of the sheath above a predefined threshold amount as the sheath moves relative to an exit ramp of the endoscope.

In one aspect of the invention, the component includes a heat shrink material located around a distal section of the flexible sheath. The heat shrink is configured to make contact with a proximal end of the exit ramp and stop longitudinal motion of the sheath. When the longitudinal motion has stopped due to the heat shrink directly contacting with the proximal end of the exit ramp, the distal end of the sheath extends beyond the working channel of the endoscope by a predefined amount.

In another aspect of the invention, a longitudinal force required to move the sheath and the heat shrink through the exit ramp is greater than a longitudinal force needed to move the sheath and the heat shrink when the heat shrink is located proximally or distally of the exit ramp.

In still another aspect of the invention, the heat shrink has a proximal geometry that makes contact with a distal end of the exit ramp. When the proximal geometry of the heat shrink makes contact with the distal end of the exit ramp, the distal end of the sheath extends beyond the working channel of the endoscope by a predefined amount.

In yet another aspect of the invention, the component includes a laser cut hypotube that includes a distal section having a first flexibility value and a proximal section having a second flexibility value. The first flexibility value is greater than the second flexibility value.

In a further aspect of the invention, a longitudinal force required to move the sheath and the proximal section of the hypotube through the exit ramp is greater than a longitudinal force needed to move the sheath and the distal section of the hypotube through the exit ramp.

In yet further aspects of the invention, a longitudinal force required to move the sheath and the hypotube through the exit ramp experiences a sudden change causing a click-like feeling as the sheath and the hypotube moves relative to the exit ramp.

In still yet further aspects of the invention, the proximal section of the hypotube restricts distal movement of the sheath through the exit ramp.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-2 shows a close-up view of a distal end of the EBUS bronchoscope of FIG. 1-1;

FIG. 2 shows a partial side view of a sheath device formed in accordance with an embodiment of the present invention;

DETAILED DESCRIPTION

The following description is merely illustrative in nature and is not intended to limit the present disclosure, application, or uses. The following description explains, by way of illustration only and not of limitation, various embodiments of devices for controlling advancement of a sheath of a medical device from an endoscope. It will be appreciated that various embodiments described herein may help to simplify the process of tissue aspiration.

Figure 1:
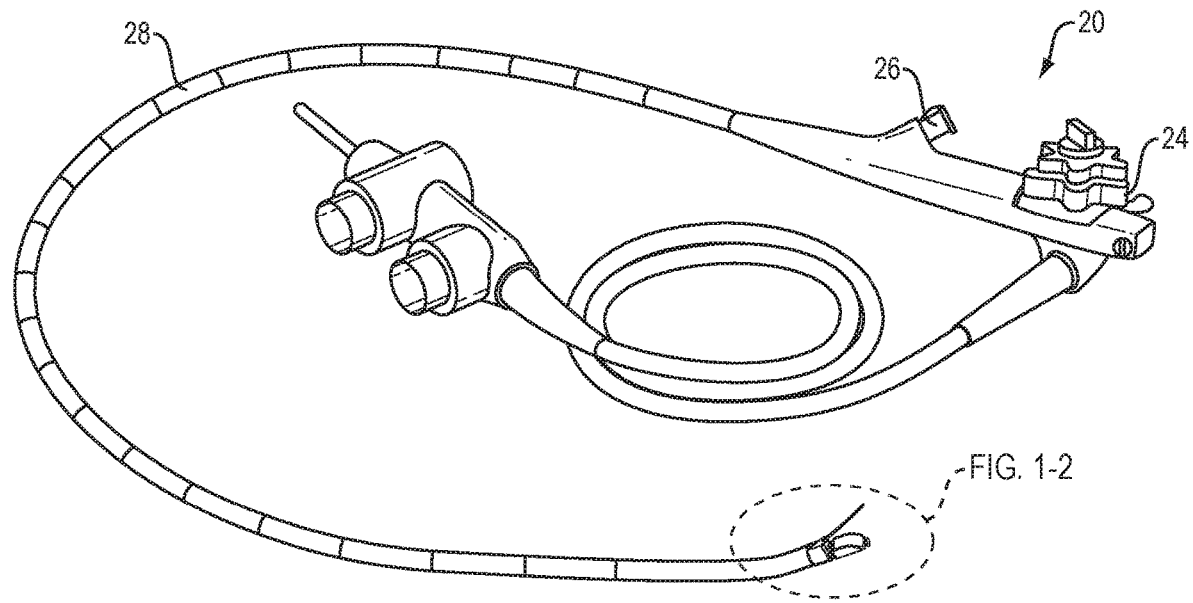
FIG. 1-1 shows a perspective view of an endobronchial ultrasound (EBUS) bronchoscope capable of receiving a sheath device formed in accordance with an embodiment of the present invention.
Figures 1, 2:
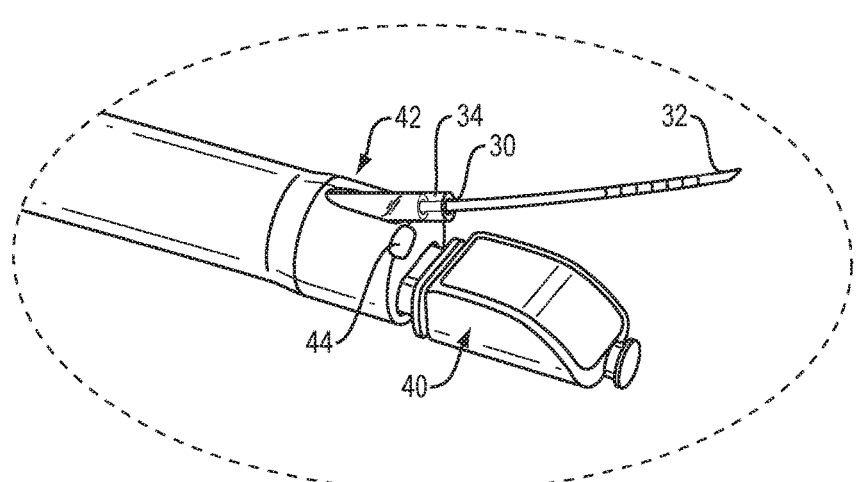
Figure 2:
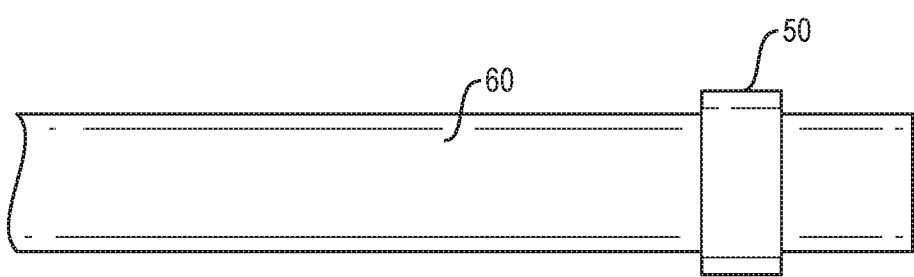

FIGS. 1-1 and 1-2 shows an exemplary endoscope (e.g., an endobronchial ultrasound (EBUS) scope 20, such as an Olympus bronchoscope UC-180F), that is capable of receiving a medical device 30 formed in accordance with embodiments of the present invention. The EBUS scope 20 includes a handle 24 with a port 26 for receiving the medical device 30 and an insertion tube 28 connected to the handle 24. A distal end of the insertion tube 28 includes an ultrasound transducer head 40, an exit port 42 for an internal lumen (i.e., working channel) that connects to the port 26, and a camera 44 with or without a light. The medical device 30 passes through the working channel to extend at least partially out of the exit port 42.

In one embodiment, the medical device 30 includes a needle 32 received within a sheath 34. The sheath 34 includes an internal feature and/or an external feature at or near its distal that will provide feedback or an enhanced physical feeling or force to an operator once that feature reaches a predefined location at or near the exit port 42 or the distal end of the working channel. This feature provides feedback to the operator which will give them an indication of where the distal end of the sheath 34 is located relative to the distal end of the working channel within the EBUS scope 20. In one embodiment, as the operator is feeding the sheath 34 through the bronchoscope, the operator will feel more pressure when the distal end of the sheath 34 is at or nearing the end of the working channel. Once the pressure is released or is noticeably reduced, then the operator knows the sheath 34 has exited the distal end of the working channel.

Figure 3:
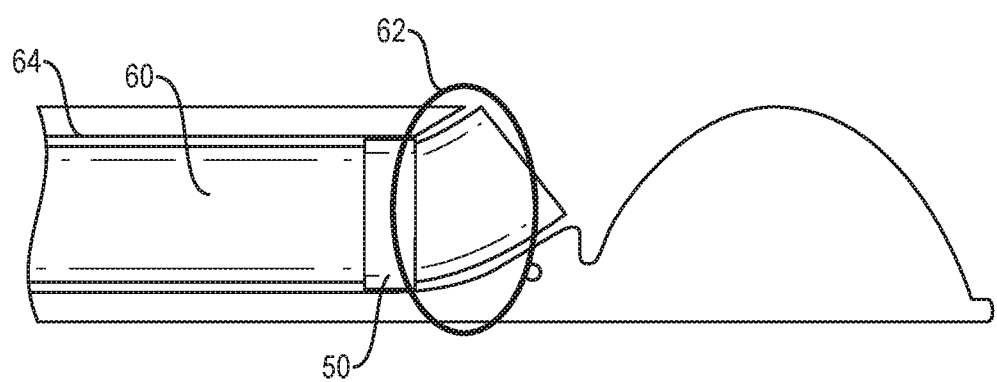
FIG. 3 shows a cross-sectional view of a portion of the sheath device of FIG. 2 positioned at a distal end of an EBUS scope.

FIG. 2 shows an exemplary sheath external feature, which includes a piece of heat shrink 50 or comparable material that adheres to a sheath 60 near the distal end. The heat shrink 50 is sized to provide feedback (i.e., increased friction) as the sheath 60, with the attached heat shrink 50, reaches a proximal end of a ramp area (exit ramp) 62 at an exit port of a working channel 64 of an EBUS scope (FIG. 3).

Figure 4:
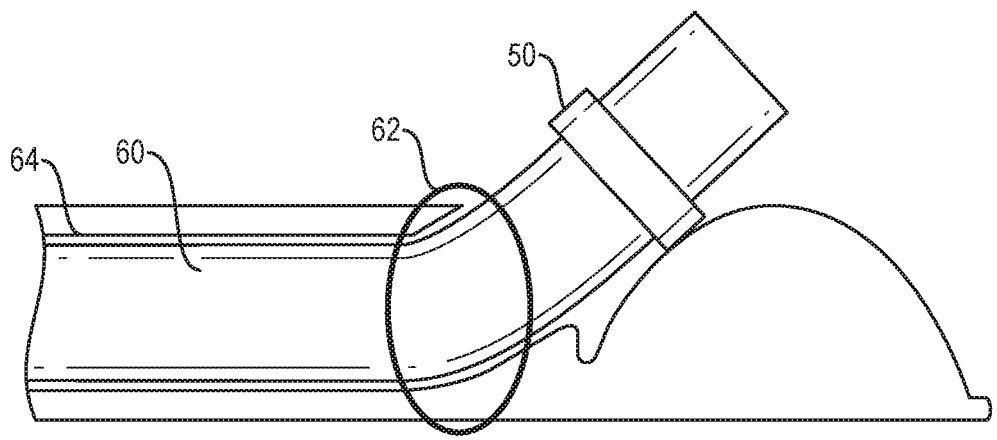
FIG. 4 shows a cross-sectional view of the portion of the sheath device of FIG. 2 at a different location relative to the EBUS scope.

As shown in FIG. 4, the sheath 60 has been advanced distally through the working channel 64 such that the heat shrink 50 has passed beyond the ramp area 62. Once the heat shrink 50 has passed beyond the ramp 62 the amount of friction (i.e., pressure) is reduced to a point where it is noticeable by an operator manually manipulating an actuator that is linked to the sheath 60 at a handle. Thus, when the operator notices the greatly reduced friction due to the heat shrink 50 passing out of the ramp 62, the operator would reduce the advancing force because they know the sheath 60 has exited the distal end of the scope.

Figure 5:
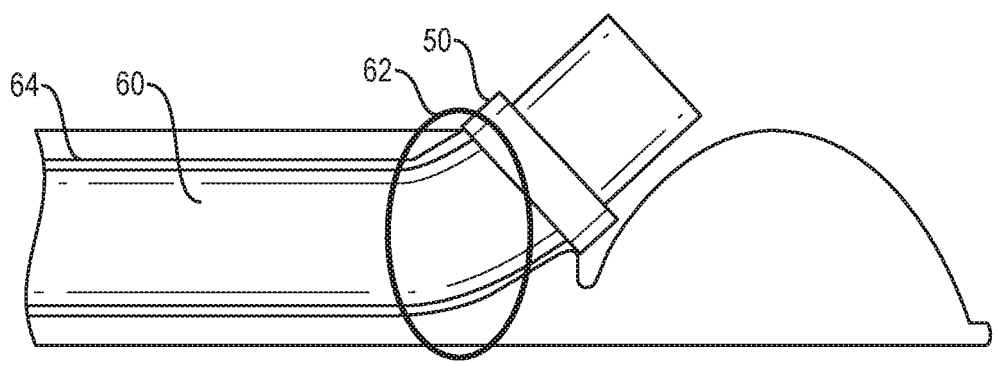
FIG. 5 shows a cross-sectional view of the portion of the sheath device of FIG. 2 at a different location relative to the EBUS scope.

As shown in FIG. 5, the sheath 60 has been retracted such that the proximal end of the heat shrink 50 makes contact with the opening of the ramp 62. When the sheath 60 is positioned as shown in FIG. 5, the distal end of the sheath 60 is properly positioned relative to the ultrasound transducer and any surrounding tissue. The operator knows that the heat shrink 50 is located at the opening of the ramp 62 when there is a change (increase) in the retraction force. This allows the operator to pull the sheath 60 back to reduce the damage risk and still know the sheath 60 is out of the working channel. A little extra force will be needed to retract the sheath 60 through the ramp and into the working channel 64.

In one embodiment, a mechanical design element(s) included in a sheath functions to aid in positioning the sheath at a predetermined set position. The mechanical design element(s) minimizes the amount of sheath protruding from the working channel and/or eliminates sheath movement associated with needle activation.

Figure 6:
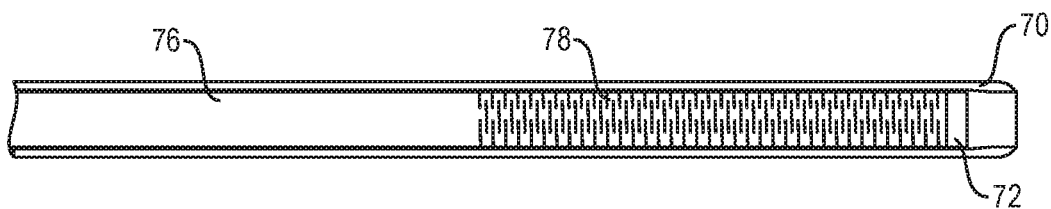
FIG. 6 shows a side x-ray view of a sheath device formed in accordance with an embodiment of the present invention.

As shown in FIG. 6, a sheath 70 includes an insert component 72 that acts as the mechanical design element. In one embodiment, the insert component 72 is a laser-cut hypotube that includes a first portion 76 and a second portion 78. The second portion 78 includes a feature(s) (e.g., etchings) that provides for increased flexibility. The first portion 76 has less or no flexibility features and is thus stiffer than the second portion 78. The stiffness value of the first portion 76 is selected to not allow the first portion 76 to extend through an exit ramp of an EBUS bronchoscope 80. In one embodiment, the stiffness value of the first portion 76 is selected to provide a discernable feedback (i.e., click into place) as the user advances the first portion 76 up to and/or through the exit ramp.

Figure 7:
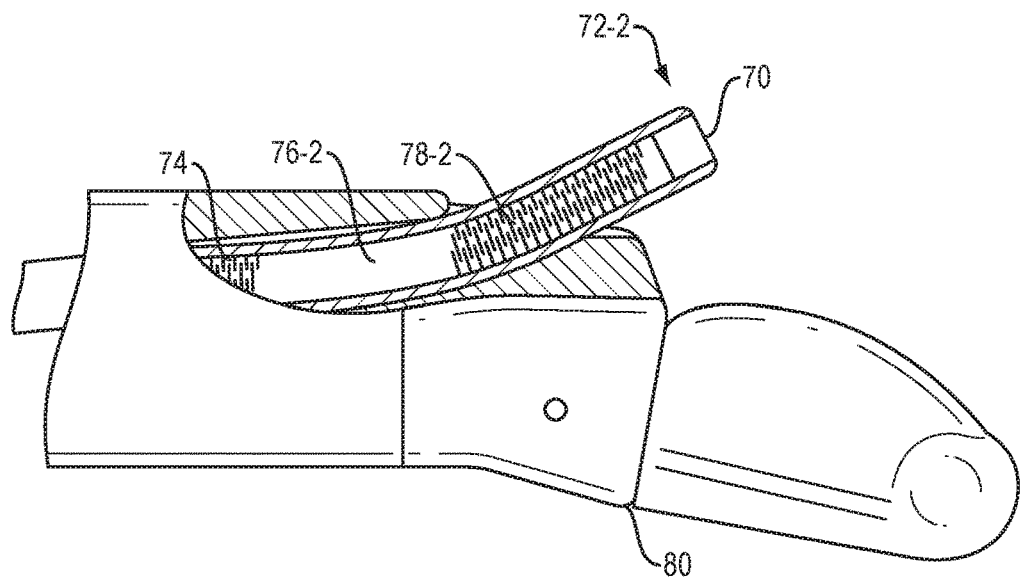
FIG. 7 shows a side, partial cross-sectional/x-ray view of a distal end of an EBUS scope with a sheath device formed in accordance with an embodiment of the present invention.

In one embodiment, as shown in FIG. 7, an insert component 72-2 includes a proximal portion 74, a distal portion 78-2 and a middle portion 76-2 located between the proximal and distal portions 74, 78-2. The proximal and distal portions 74, 78-2 include features (e.g., etchings) that provide for increased flexibility. The middle portion 76-2 has less or no flexibility features and is thus stiffer than the distal portion 78-2. The stiffness value of the middle portion 76-2 and/or the length of the middle portion 76-2 is selected to not allow the middle portion 76-2 to extend through an exit ramp of an EBUS bronchoscope 80. In one embodiment, the stiffness value of the middle portion 76-2 is selected to provide a discernable feedback (i.e., click into place) as the user advances the middle portion 76-2 up to and/or through the exit ramp. The flexible proximal portion 74 provides added protection of the scope from a needle without adding too much stiffness, by decreasing insertion forces and/or reducing issues with scope durability.

Figure 8:
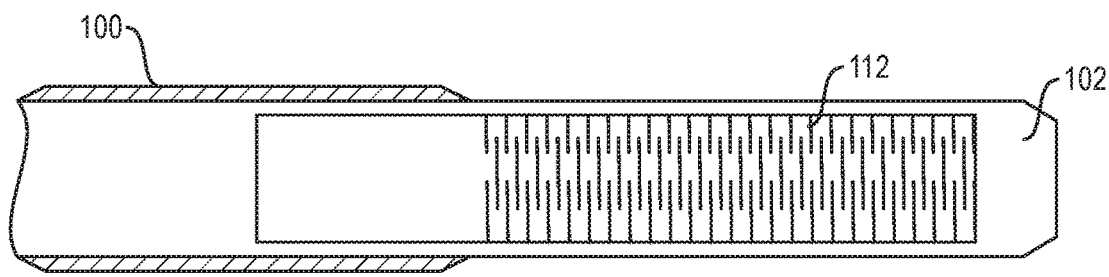
FIG. 8 shows a cross-sectional/x-ray view of a portion of a sheath device formed in accordance with an embodiment of the present invention.
Figure 9:
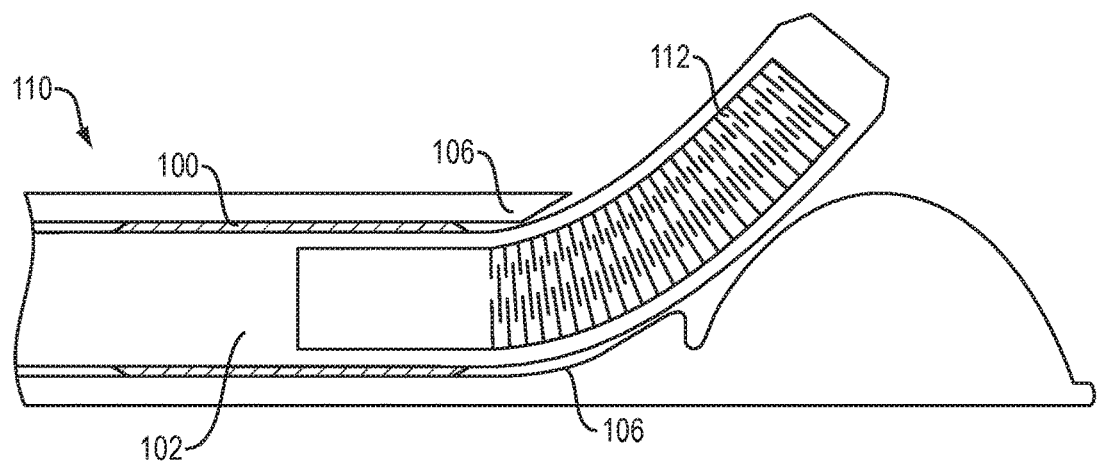
FIG. 9 shows a cross-sectional/x-ray view of a portion the sheath device of FIG. 7 received within a working channel of an EBUS scope.

As shown in FIGS. 8 and 9, a medical device includes a heat shrink collar 100 that is placed around a sheath 102 at a distal end. The heat shrink collar 100 is offset from the distal end of the sheath 102 so that when the sheath 102 is inserted into the scope, the sheath 102 extends outside of the scope when the heat shrink collar 100 catches at a ferrule/ramp 106 inside a scope 110. In one embodiment, the sheath 102 does not extend into a field of view of a camera (~2 mm). The heat shrink 100 has a predefined length, width, and stiffness in order for the sheath 102 to catch at the base of the ramp 106. The stiffness caused by the heat shrink 100 is not too stiff to prevent the medical device from getting around other bends of the scope 110 and has a low to non-existent risk of getting wedged into the ramp 106. In one embodiment, the edges of the heat shrink 100 are reflowed to prevent unwanted damage to the scope 110. A certain geometric shape of the edges of the heat shrink 100 may be beneficial for catching the medical device at the base of the ramp 106 and thus preventing overextension of the sheath 102 in the distal direction and providing a location guide in the proximal direction after extension.

The sheath 102 may also include a sheath insert 112 inserted into the distal end. The sheath insert 112 protects the scope when a needle (not shown) is received within the sheath 102. The heat shrink 100 may be located proximally from the sheath insert 112 or may partially overlap the sheath insert 112. Any of the sheath inserts/insert components may be a laser cut hypotube or comparable material.

Embodiments

A. An apparatus comprising: a flexible sheath configured to receive a medical device within an internal lumen and configured to be received within a working channel of an endoscope; and a component received at least one of externally on or internally within the sheath, the component configured to cause a change in longitudinal motion friction of the sheath above a predefined threshold amount as the sheath moves relative to an exit ramp of the endoscope.

B. The apparatus of B, wherein the component comprises a heat shrink material located around a section of the flexible sheath.

C. The apparatus of C, wherein the heat shrink is configured to make contact with a proximal end of the exit ramp and stop longitudinal motion of the sheath.

D. The apparatus of C, wherein when the longitudinal motion has stopped due to the heat shrink directly contacting with the proximal end of the exit ramp, the distal end of the sheath extends beyond the working channel of the endoscope by a predefined amount.

E. The apparatus of B, wherein a longitudinal force required to move the sheath and the heat shrink through the exit ramp is greater than a longitudinal force needed to move the sheath and the heat shrink when the heat shrink is located proximally or distally of the exit ramp.

F. The apparatus of any of A-E, wherein the heat shrink is configured to have a proximal geometry configured to make contact with a distal end of the exit ramp.

G. The apparatus of F, wherein when the proximal geometry of the heat shrink makes contact with the distal end of the exit ramp, the distal end of the sheath extends beyond the working channel of the endoscope by a predefined amount.

H. The apparatus of A, wherein the component comprises a laser cut hypotube, the laser cut hypotube comprises: a distal section having a first flexibility value; and a proximal section having a second flexibility value, wherein the first flexibility value is greater than the second flexibility value.

I. The apparatus of H, wherein a longitudinal force required to move the sheath and the proximal section of the hypotube through the exit ramp is greater than a longitudinal force needed to move the sheath and the distal section of the hypotube through the exit ramp.

J. The apparatus of H, wherein a longitudinal force required to move the sheath and the hypotube through the exit ramp experiences a sudden change causing a click-like feeling as the sheath and the hypotube moves relative to the exit ramp.

K. The apparatus of H, wherein the proximal section of the hypotube restricts distal movement of the sheath through the exit ramp.

The description of the invention is merely exemplary in nature and variations that do not depart from the gist of the invention are intended to be within the scope of the invention. Such variations are not to be regarded as a departure from the spirit and scope of the invention.

Although the preferable embodiments of the present invention have been described hitherto, the present invention is not limited to these embodiments. Additions, omissions, substitutions, and other modifications can be made without departing from the spirit or scope of the present invention.

In addition, the invention is not limited by the above description and is limited only by the scope of appended claims.

What is claimed is:

1. An apparatus comprising:
   an endoscope including a working channel, the working channel including a bend in a portion of the working channel adjacent an opening in a distal end of the working channel forming an exit area, the exit area configured to direct a medical instrument out of the working channel at an angle relative to a longitudinal axis of the working channel;
   a flexible sheath configured to receive the medical instrument within an internal lumen and configured to be received within the working channel of the endoscope; and
   a component received externally adjacent a distal end of the sheath and positioned to provide feedback to a user regarding a position of a distal end of the flexible sheath relative to the exit area in the distal end of the working channel, the component includes an external dimension sized to generate an increase in friction upon interaction with the bend in the exit area upon extension of the flexible sheath out of the endoscope and with the opening associated with the exit area upon retraction of the flexible sheath into the endoscope.

2. The apparatus of claim 1, wherein the endoscope comprises an endobronchial ultrasound bronchoscope.

3. The apparatus of claim 1, wherein the component is a short segment of heat shrink material applied around a section of the flexible sheath adjacent a distal end of the flexible sheath.

4. The apparatus of claim 3, wherein the short segment of heat shrink material is configured to make contact with a distal end of the exit area and restrict longitudinal motion of the sheath as it is retracted back into the working channel.

5. The apparatus of claim 4, wherein when the longitudinal motion is restricted due to the short segment of heat shrink material directly contacting with the distal end of the exit area, a distal end of the sheath extends beyond the working channel of the endoscope by a predefined amount.

6. The apparatus of claim 3, wherein the short segment of heat shrink material is configured to have a proximal geometry configured to make contact with a distal end of the exit area.

7. The apparatus of claim 6, wherein when the proximal geometry of the short segment of heat shrink material makes contact with a distal end of the exit area, the distal end of the sheath extends beyond the working channel of the endoscope by a predefined amount.

8. An apparatus comprising:
   an ultrasound device including a working channel and an ultrasound sensor, the working channel including a bent distal portion forming an exit ramp at the distal end of the working channel, the exit ramp configured to direct a medical instrument out of the working channel at an angle relative to a longitudinal axis of the working channel and the ultrasound sensor disposed distally from a distal end of the exit ramp;
   a sheath configured to receive the medical instrument within an internal lumen and configured to be received within the working channel of the ultrasound device; and
   a component received externally adjacent a distal end of the sheath, the component including an external dimension sized to generate an increase in friction upon interaction with the bent distal portion forming the exit ramp of the ultrasound device to provide feedback during extension of the sheath out of the working channel indicative of a position of the distal end of the sheath relative to the ultrasound sensor.

9. The apparatus of claim 8, wherein the component includes a proximal shoulder configured to engage with the distal end of the exit ramp to provide feedback to a user regarding a position of the sheath upon retraction of the sheath into the working channel.

10. The apparatus of claim 8, wherein the component is a short cylindrical segment of heat shrink material disposed a pre-defined distance proximal of the distal end of the sheath.

11. The apparatus of claim 10, wherein the short cylindrical segment of heat shrink material is configured to make contact with a distal end of the exit ramp and restrict longitudinal motion of the sheath as it is retracted back into the working channel.

12. The apparatus of claim 11, wherein when the longitudinal motion is restricted due to the short cylindrical segment of heat shrink material engaging the bent distal portion forming the exit ramp, a distal end of the sheath extends beyond the working channel by a predefined amount.

13. The apparatus of claim 10, wherein a longitudinal force required to move the sheath and the short cylindrical segment of heat shrink material through the exit ramp is greater than a longitudinal force needed to move the sheath and the short cylindrical segment of heat shrink when the short cylindrical segment of heat shrink is located proximally or distally of the exit ramp.

\* \* \* \* \*